United States Patent [19]

Gresko

[11] 4,014,398
[45] Mar. 29, 1977

[54] WEIGHT DISTRIBUTION MEASURING INSTRUMENTS

[76] Inventor: William Gresko, 17837 107th Ave., Sun City, Ariz. 85351

[22] Filed: July 7, 1975

[21] Appl. No.: 593,429

[52] U.S. Cl. .............................. 177/208; 177/254; 128/2 S
[51] Int. Cl.² ...................... G01G 5/04; A61B 5/10
[58] Field of Search .......... 177/208, 209, 254, 245; 128/2 S

[56] References Cited
UNITED STATES PATENTS

| | | | |
|---|---|---|---|
| 2,043,187 | 6/1936 | Owens | 177/245 UX |
| 2,095,268 | 10/1937 | Roberts | 177/209 X |
| 2,313,156 | 3/1943 | Kratt, Jr. | 177/208 X |
| 3,305,036 | 2/1967 | Walters | 177/208 X |
| 3,433,316 | 3/1969 | Newman | 177/208 |

*Primary Examiner*—George H. Miller, Jr.
*Attorney, Agent, or Firm*—Joseph A. Fenlon

[57] ABSTRACT

Weight Distribution Measuring Instruments which provide accurate simultaneous readings showing how a patient's weight is distributed between the heels and balls of his feet whereby to provide clinical information to a physician as to whether or not an injury causes that patient to favor one leg or one portion of his leg unconsciously; this is accomplished by providing a base with two separate pairs of foot pads, one pair for each heel and ball of each foot, and by making the heel and ball positions mechanically adjustable with respect to each other to compensate for variations in foot size; a separate read out gauge is provided for and hydraulically coupled to each foot pad to provide an accurate reading of the weight presented to each pad; valves are provided to lock the readings of the gauges at any selected time.

3 Claims, 14 Drawing Figures

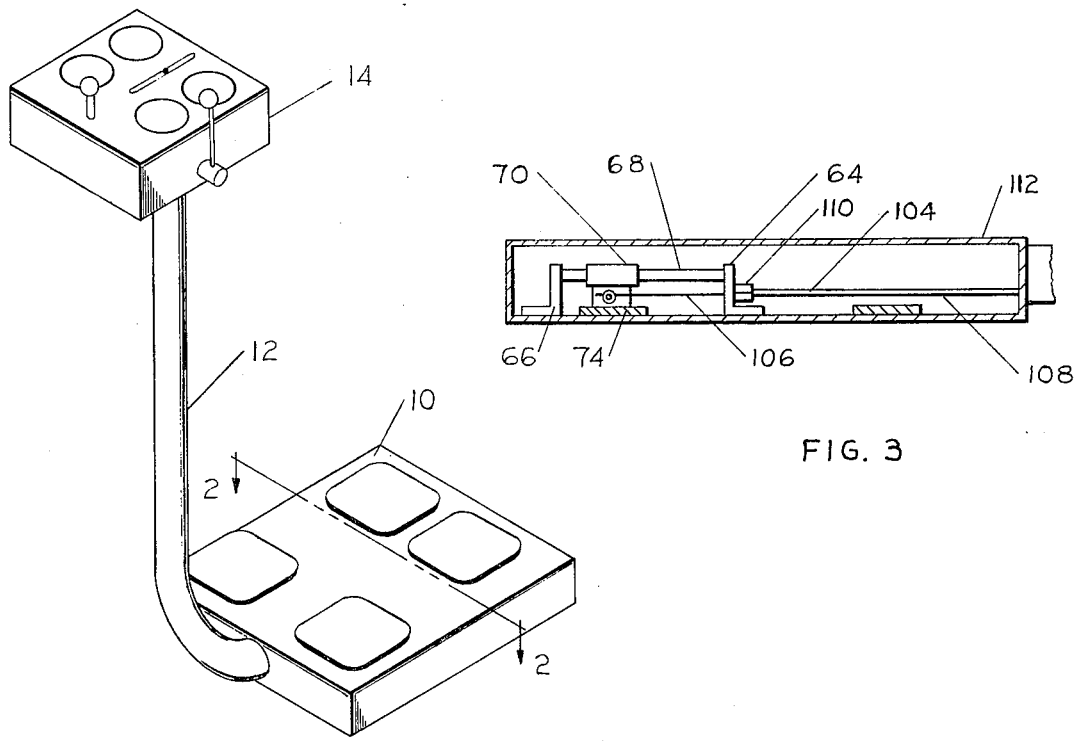
FIG. 3
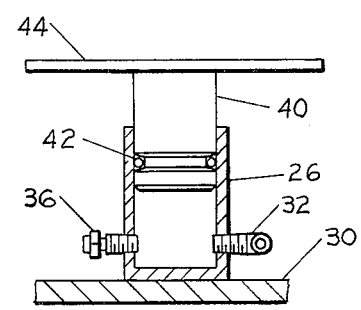
FIG. 4
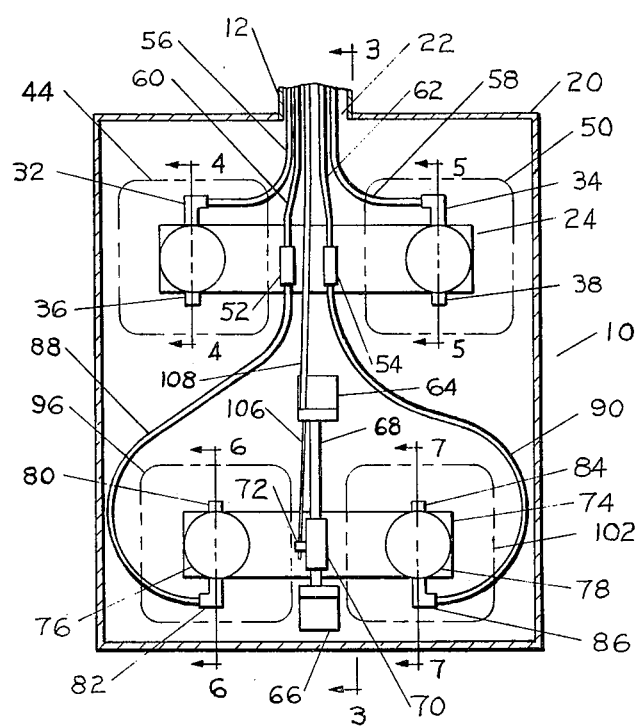
FIG. 1
FIG. 2

WEIGHT DISTRIBUTION MEASURING INSTRUMENTS

It is the object of this invention to provide an accurate measuring instrument to measure the manner in which a patient's weight is distributed throughout the weight bearing portions of his feet.

With the above and other objects in view which will become immediately apparent upon reading the specification and inspecting the drawings, my invention resides in the unique and novel form, construction, arrangement and combination of the various parts described in the specification, shown in the drawings and claimed in the claims.

IN THE DRAWINGS

FIG. 1 is a perspective view of a device embodying my invention.

FIG. 2 is an enlarged sectional view of the base taken along lines 2—2 of FIG. 1.

FIG. 3 is a fragmentary sectional view taken along lines 3—3 of FIG. 2.

FIGS. 4–7 are enlarged fragmentary sectional views taken along lines 4—4, 5—5, 6—6 and 7—7 respectively of FIG. 2.

Figure 5:
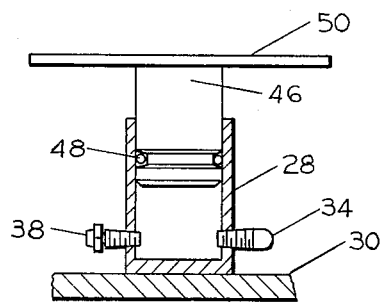
Figure 6:
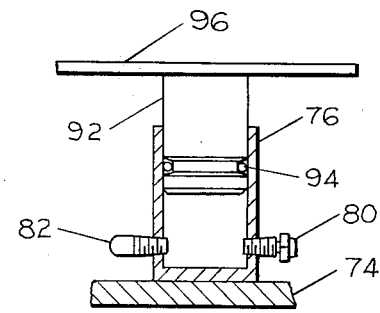
Figure 8:
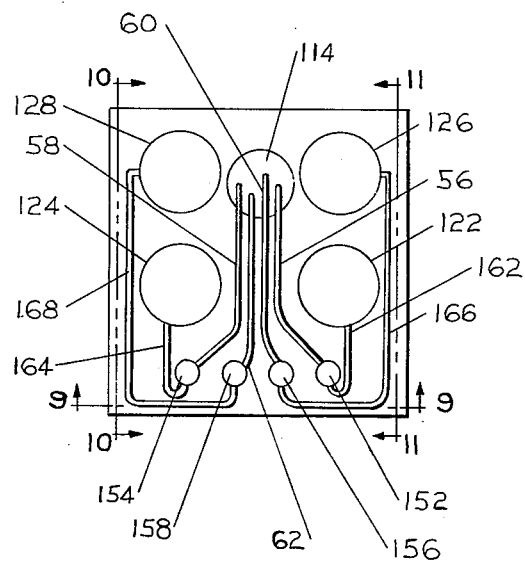
FIG. 8 is a top plan view of the inside of the master control panel showing hydraulic line distribution only for purposes of clarity.
Figure 7:
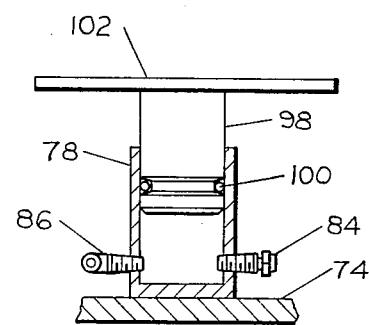
Figure 9:
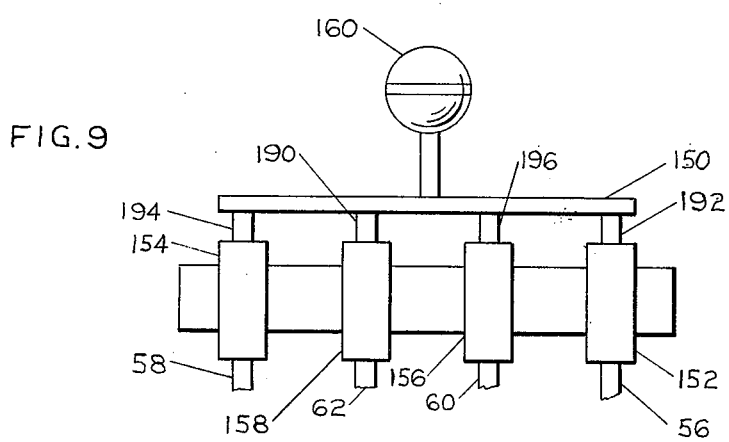
FIG. 9 is an enlarged fragmentary sectional view taken along lines 9—9 of FIG. 8.
Figure 10:
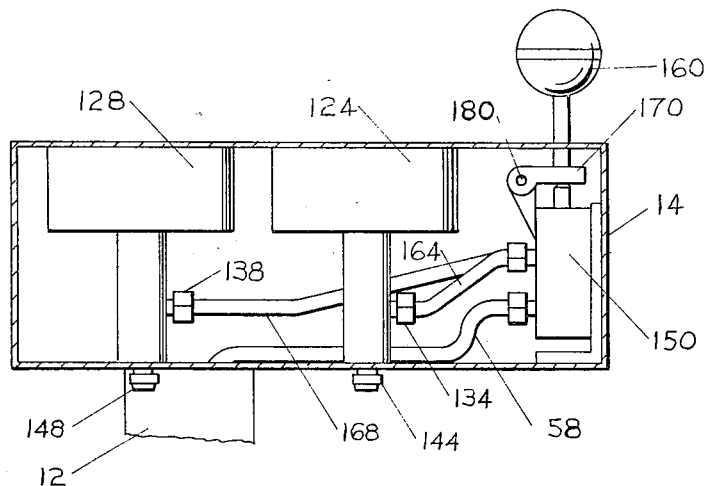
Figure 11:
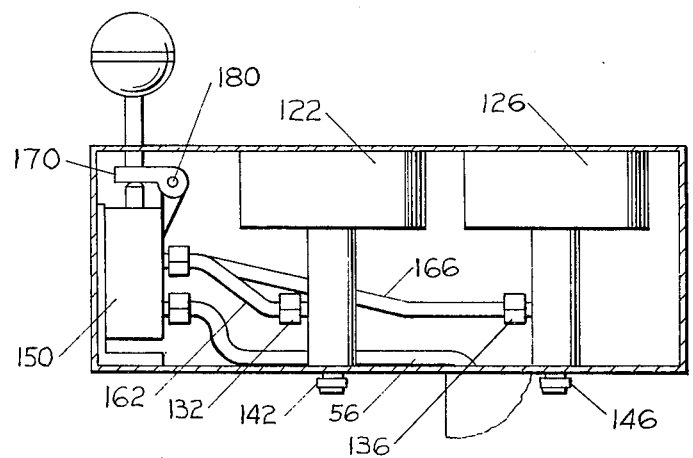

FIGS. 10 and 11 are fragmentary sectional views with mechanical shoe size linkages removed from clarity taken along lines 10—10 and 11—11 respectively of FIG. 8.

Figure 12:
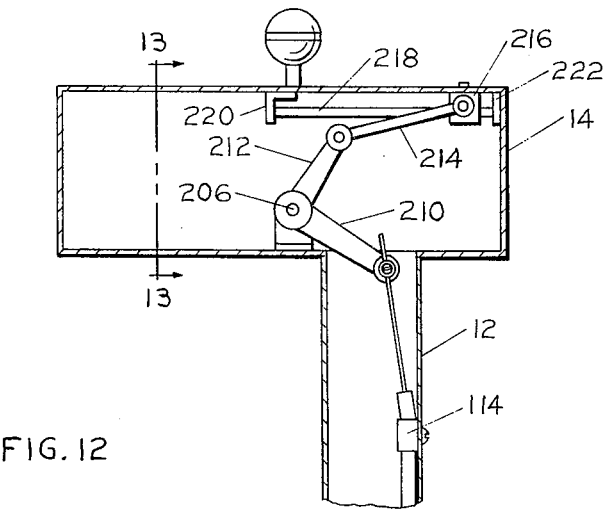

FIG. 12 is a fragmentary sectional view taken along lines 10—10 of FIG. 8 with hydraulic gauges and lines removed for clarity.

Figure 13:
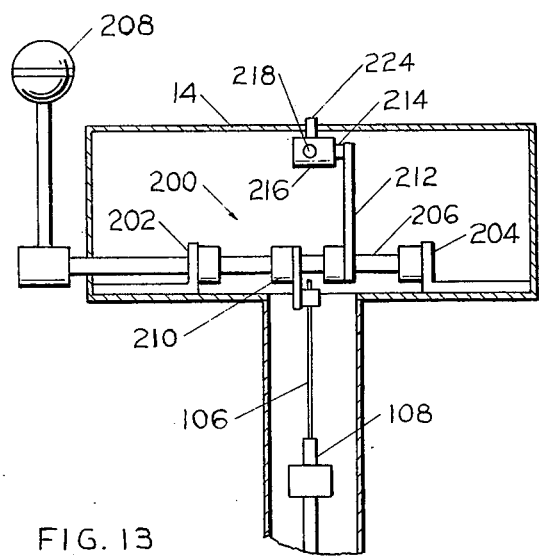

FIG. 13 is a fragmentary sectional view taken along lines 13—13 of FIG. 12.

Figure 14:
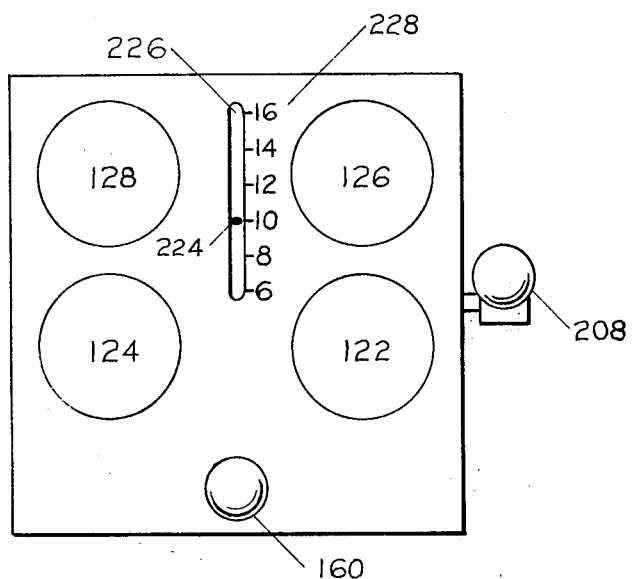

FIG. 14 is a top plan view of the face of the control panel.

Referring now in more detail and by reference character to the drawings which illustrate a preferred embodiment of my invention, A designates a weight distribution measurement device comprising a base 10, a vertically extending tubular post 12 and an instrument housing 14.

The base 10 comprises a rectangular housing 20 provided along one lateral wall with an access opening 22 to which the post 12 is secured. Secured to the housing 20 in spaced separation from each other adjacent to opening 22 is a cylinder support assembly 24 which includes with upwardly extending hydraulic cylinders 26, 28, joined by an intermediate connecting bar 30.

The cylinders 26, 28, are respectively provided near their respective bottoms thereof with hydraulic tube connectors 32, 34, and conventional bleeder fittings 36, 38. Movably disposed in the cylinder 26 is a piston 40 provided adjacent its lower end with an O-ring fitting 42 and at its upper end with a foot pad 44. Similarly, movably disposed in the cylinder 28 is a piston 46 provided adjacent its lower end with an O-ring 48 and at its upper end with a foot pad 50. Mounted on the connecting bar 30, are hydraulic tube couplings 52, 54. Respectively connected to the connectors 32, 34, and the couplings 52, 54 and extending through the opening 22 into the interior of the post 12 are one end of hydraulic fluid lines 56, 58, 60 and 62.

Secured to the housing 20 rearwardly of the cylinders 26, 28 are spaced brackets 64, 66, between which is securely disposed a guide rod 68. Slidably mounted on the guide rod 68 is slide member 70 provided with a choke wire attachment fitting 72 and secured at its base to an elongated flat cross member 74 on which are mounted, in spaced separation from each other, hydraulic cylinders 76, 78, the cylinder 76 being provided with a bleed valve 80 and an hydraulic line coupling 82, and the cylinder 78 being provided with a bleed valve 84 and an hydraulic line coupling 86. Disposed in the housing 20 and coupled to the couplings 52, 82, is a flexible hydraulic line 88.

Similarly disposed in the housing 20 and coupled to the couplings 54, 86, is a second flexible hydraulic line 90. Movably disposed in the cylinder 76 is a piston 92 provided adjacent its lower end with an O-ring 94 and at its upper end with a foot pad 96. Similarly, movably disposed in the cylinder 78 is a piston 98 provided at its lower end with an O-ring 100 and at its upper end with a foot pad 102. Extending through the post 12 and into the housing 20 is one end of a choke wire assembly 104 comprising a slide wire 106 movably disposed in a sleeve 108, the wire 106 being secured to the attachment fittings 72 and the sleeve 108 being secured to the bracket 64 by a set screw attachment 110 on the bracket 64.

It should be apparent that movement of the slide wire 106 with respect to the sleeve 108 causes the slide member 70 to move on the rod 68 which causes the foot pads 96 and 102 to move longitudinally toward and away from the foot pads 44 and 50 all for purposes presently more fully to appear.

It should also be noted that the upper face 112 of the housing 20 is provided with apertures through which the pistons 40, 46, 92 and 98 project, the apertures for the pistons 92 and 98 being slotted so as not to constrict the longitudinal forward and rearward movement of the slide member 70.

The tubular post 12 is attached at one end to the base 10 at the opening 22 and at the other end to the instrument housing 14 near an opening 114. The lines 56, 58, 60 and 62 and the choke wire assembly 104 are routed from the base 10 to the instrument housing 14 through the interior of the post 12. Near the upper end of the post 12, the other end of the sleeve 108 of the choke wire assembly 104 is secured to the post 12 by a clamp 114 and the slide wire 106 extends through the opening 114 into the housing 14.

Mounted on the upper face of the instruments housing 14 are four hydraulic measurement gauges 122, 124, 126, 128, each calibrated in pounds and each respectively provided with hydraulic line attachment couplngs 132, 134, 136, 138, and bleed valves 142, 144, 146, 148. Also mounted in the housing 14 is a master check valve assembly 150 which includes four independent check valves 152, 154, 156, 158, each respectively coupled at their input connections to the lines 56, 58, 60, 62, and each respectively coupled at their output connections to the gauges 122, 124, 126, 128 through hydraulic lines 162, 164, 166, 168.

The master check valve assembly 150 is conventional and provides for simultaneous independent opening of the four valves 152, 154, 156, 158 by movement of a handle 160 to one position and simultaneous independent closing of the four valves 152, 154, 156, 158 by return movement of the handle 160 to the original position. A typical though nor necessarily the only way of providing this type of control is by selecting the valves 152, 154, 156, 158 to be spring biased, normally closed valves each having upwardly projecting pistons 192, 194, 196, 198 which abut the bottom of a bracket 170 to which the handle 160 is attached and which is pivotally attached to the assembly 150 by a hinge 180. Pivotal movement of the handle 160 causes simultaneous depression of the pistons 192, 194, 196, 198 thereby opening the valves 152, 154, 156, 158. Release of the handle 160 causes the valves 152, 154, 156, 158 to close automatically because of the self-contained spring bias.

Also mounted in the housing 14 is a foot pad adjusting control 200, comprising a pair of spaced bearings 202, 204 mounted in the housing 14; a rod 206 rotationally mounted in the bearings 202, 204; a control handle 208 secured to the rod 206; a first linkage arm 210 secured to the rod 206 at one end and to the slide wire 106 at the other end; and a second linkage arm 212 secured at one end to the rod 206. Pivotally attached to the other end of the second linkage arm 212 is a connecting rod 214 which is pivotally attached to a slide 216 movably disposed on a bar 218 which is held securely on the upper portion of the housing 14 by brackets 220, 222, which are secured to the housing 14. The slide 216 also is provided with an upwardly projecting indicator tip 224 which projects through an elongated slot 226 in the upper surface of the housing 14 intermediate the gauges 122, 124, 126, 128. On the upper face of the housing 14 adjacent the slot 226, an indicator strip 228 is mounted which is calibrated in shoe sizes from 6 through 16.

OPERATION

The instrument A is placed in condition for operation by first adjusting the relative position of the foot pads 44, 50, 96, 102, to conform to the patient's feet. This is done by moving the handle 208 which causes the slide wire 106 to move in the choke wire assembly 104, in tune causing the bracket 70 to move along the guide rod 68, whereby causing the foot pads 96, 102 to be selectively positioned with respect to the fixed foot pads 44, 50. The indicator tip 224 indicates on the strip 228 the selected shoe size positioning of the pads 96, 102, with respect to the foot pads 44, 50.

With the rod 206 in the selected setting, the master check valve control 150 is opened causing direct hydraulic communication between the foot pad 44 and the gauge 122, the foot pad 50 and the gauge 124, the foot pad 96 and the gauge 126, and the foot pad 102 and the gauge 128. A quick visual check confirms the zero reading of the gauges 122, 124, 126, 128 in the no-load condition and the patient is then instructed to position himself on the scale with his heels on the foot pads 96, 102, and the balls of his feet on the foot pads 44, 50. After the patient has positioned himself on the base 10 for sufficient time for the readings of the gauges 122, 124, 126, 128 to stabilize, the master check valve control 150 is closed by release of the handle 160 and the readings of the gauges 122, 124, 126, and 128 are "frozen" until the patient has removed himself from the base 10 and the handle 160 has again been depressed which releases the pressure of the fluid trapped in the tubes 162, 164, 166, 168. After the readings of the gauges 122, 124, 126 and 128 have been recorded to show weight distribution on the heels and balls of the patient's feet, the readings may be then removed by again actuating the handle 160.

Excess air is removed from the system by forcing hydraulic fluid into one of the bleed valves 36, 38, 80, 84 and continuing forced flow of such fluid until air ceases to bubble out of the respective complimentary bleed valves 142, 144, 146, 148 at the other end of the particular hydraulic system.

It should be understood that changes, alterations and modifications in the form, construction, arrangement and combination of the various parts may be made and substituted for those herein shown and described without departing from the operation and principles of my invention.

Having thus described my invention, what I claim and desire to secure by Letters Patent is stated in the following Claims:

1. A weight distribution measuring device comprising a base, first and second pairs of foot pads mounted on said base, adjustable means for horizontally positioning the first pair of foot pads with respect to said second pair of foot pads on said base, weight responsive means operatively connected to each of the food pads for independently measuring the amount of weight present on each of the foot pads, and metering means for presenting simultaneously the amount of weight present on each of the foot pads, the first pair of foot pads being in fixed position with respect to the base and the second pair of foot pads being mounted on the base for forward and rearward movement with respect to the first pair of pads, each of the pads being operatively disposed on the piston of a hydraulic cylinder, which said cylinder is hydraulically connected through locking means to a gage mounted on a display panel and calibrated to give a direct read-out of the weight presented to the respective pad, and the locking means including a four way hydraulic control valve adapted for establishing hydraulic communication between the cylinder of each pad and the respective gage when the control valve is in the "open" position and for retaining the reading presented to each gage when the control valve is in the closed position.

2. The device of claim 1 wherein the adjustable means includes a choke wire comprising a sleeve and a slide wire slidably mounted therein, the sleeve is secured to the base, the slide wire is connected at one end to a support means slidably in the base for supporting the first pair of pads, and the other end of the slide wire is attached to a lever pivotally mounted in the control panel for selectively varying the separation between the first pair of pads and the second pair of pads.

3. A weight distribution and measuring device comprising a housing, a pair of heel pads mounted in the housing in spaced separation from each other and being fixedly disposed therein, a pair of sole pads adjustably disposed in spaced separation from each other in said housing, means for selectively adjusting the horizontal separation between the sole pads and the heel pads, sensing means operatively connected to each of the pads for sensing the amount of weight present thereon, positioning means for selectively positioning the sole pads with respect to the heel pads, and indicia means for identifying the amount of weight supported by each of said pads, said positioning means includes a choke wire comprising a sleeve and a slide wire slideably mounted therein, the sleeve being secured to the housing, and the slide wire being secured at one end to the two sole pads and at the other end to a control handle pivotally mounted on the housing and adapted for causing the slide wire to move with respect to the sleeve when the handle is moved with respect to the housing.

* * * * *